United States Patent [19]

Stief

[11] Patent Number: 5,214,030

[45] Date of Patent: May 25, 1993

[54] CALCITONIN GENE-RELATED PEPTIDES FOR TREATING ERECTILE DYSFUNCTIONS

[76] Inventor: Georg Stief, Rehmenbreiten 6, D-3005 Hemmingen-Westerfeld, Fed. Rep. of Germany

[21] Appl. No.: 761,969

[22] PCT Filed: Apr. 21, 1990

[86] PCT No.: PCT/EP90/00644

§ 371 Date: Oct. 18, 1991

§ 102(e) Date: Oct. 18, 1991

[87] PCT Pub. No.: WO90/12586

PCT Pub. Date: Nov. 1, 1990

[30] Foreign Application Priority Data

Apr. 27, 1989 [DE] Fed. Rep. of Germany ....... 3913954

[51] Int. Cl.[5] .................... A61K 37/00; A61K 37/30; C07K 5/00; C07K 7/00

[52] U.S. Cl. ........................................ 514/12; 514/9; 514/11; 530/307; 530/324

[58] Field of Search ............... 514/9, 11, 12; 530/307, 530/324, 317

[56] References Cited

PUBLICATIONS

Stief et al., J. Urology, vol. 143, pp. 392–397, Feb. 1990.
Stief et al., J. Urology, vol. 146, pp. 1010–1014, Oct. 1991.
Iwanaga et al., Biological Abstracts, vol. 81, No. 8, Ref. No. 78180.

Primary Examiner—Lester L. Lee
Assistant Examiner—A. M. Davenport
Attorney, Agent, or Firm—Mason, Fenwick & Lawrence

[57] ABSTRACT

A method of treating erectile dysfunctions in mammals and men, by administering to the mammal or man a pharmaceutical composition comprising a therapeutically effective amount of a calcitonin gene-related peptide.

7 Claims, No Drawings

CALCITONIN GENE-RELATED PEPTIDES FOR TREATING ERECTILE DYSFUNCTIONS

BACKGROUND OF THE INVENTION

1. Field of the Invention

The present invention is concerned with the use of calcitonin gene-related peptides and of the analogues thereof for the treatment of erectile dysfunctions.

2. Description of the Prior Art

Calcitonin gene-related peptides are known and are described, for example, in published European Patent Specification No. 0,212,432 and in U.S. Pat. Nos. 4,530,838 and 4,687,839, but such peptides are described therein as having actions on memory, sensitivity to pain, and lowering of the blood pressure, and or the secretion of gastric juices.

About 5% of men in the 40th year of their life and 20% in the 60th year of their life suffer from an erectile dysfunction. Due to the loss of potency, the bodily, psychological and social self-assurance of men and especially of young men is shaken. Patients with chronic erectile dysfunction are made uncertain in their sexuality and personality and are to be regarded as being ill.

Until the 1970's, potency disturbances were attributed to psychogenic causes, and were thus treated with psychotherapeutic measures as well as testosterone and aphrodisiacs of debatable value. Only after investigation of the physiology of erection was it ascertained that, in the case of more than 60% of the patients, organic causes bring about the disturbance of the erection, in which autonomic efferences from the parasympathetic part of the sacral centre, neurotransmitters, dilation of the penile arteries, relaxation of the cavernosal spaces and constriction of the veins play a part. In more than 70% of the cases, vascular factors originally participated, such as pathological arterial blood supply or abnormally increased venous drainage from the cavernosal spaces. Neurogenic disturbances are involved in about 20% of the cases.

The oral therapy of these organically caused dysfunctions with vasoactive substances, such as yohimbine, phenoxybenzamine, terbutaline, bethanechol, levodopa, verapamil or theophylline proved to be useless. Besides the use of prosthetic implants or of revascularization operations, an intracavernosal injection of papaverine (Virag, Lancet, 2, 938, 1982), of the α-receptor blocker phenoxybenzamine (Brindley, Br. J. Psychiatr., 143, 332/1983) and of a combination of papaverine and the α-receptor blocker phentolamine (Stief, Urologe A, 25, 63/1986) proved to be successful. The latter therapeutic method can be carried out by the patients themselves and is referred to as erectile tissue autoinjection therapy.

However, a sometimes undesired prolonged erection with the danger of priapism in the case of the use of papaverine, undesired pain in the case of the use of phenoxybenzamine, as well as the possible cancerogenesis of this compound, proved to be disadvantageous.

In animal experiments (Cynomolgus monkey), in the case of 1-2 intracavernosal injections of papaverine per week over a period of 12 months, extensive fibrous formation in further parts of the erectile tissue were ascertained which, in the case of humans, would lead to extremely negative long-term results since, in the case of a fibrous formation in the corpus cavernosum, an erection can no longer be achieved.

The use of acetylcholine is, in the case of only a brief period of erection, associated with strong systemic side effects and the injection of prostaglandin $E_1$ is refused by patients because of the intense pain caused by this drug.

SUMMARY OF THE INVENTION

Therefore, it is an object of the present invention to develop and prepare pharmaceutical compositions for the treatment of neurogenic, arterial, neurotransmitter-caused, myopathic, venous or psychogenic erectile dysfunctions in mammals, especially in men, without the occurrence of the above-mentioned side effects.

Surprisingly, we have found that the intracavernosal injection of a peptide natural to the body of the formula (I):

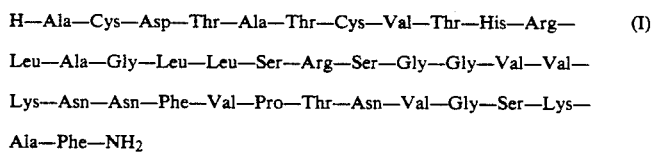

the structure of which is coded by alternative splicing of the calcitonin gene, i.e. a so-called "calcitonin gene-related peptide" (CGRP), which displays strong vasodilatory properties, results in an erection. Since, in addition, the human calcitonin gene-related peptide (h-CGRP) occurs ubiquitously in the organism, the therapeutic use of this peptide is possible without the danger of a subsequent fibrous formation.

DESCRIPTION OF THE PREFERRED EMBODIMENTS

Therefore, the present invention is concerned with the use of calcitonin gene-related peptides, hereinafter referred to as CGRP, of the analogues thereof, and of these peptides as partial sequences of a larger peptide or as a total sequence, preferably of the amino acid sequence of the general formula (II):

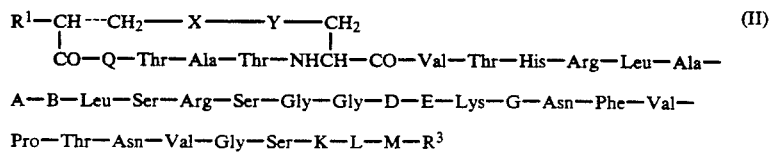

wherein $R^1$ is either a hydrogen atom or a radical of the general formula (III):

$$R^2-T- \quad (III)$$

wherein

T is Ala or Ser and $R^2$ is a hydrogen atom or an acyl radical containing up to 4 carbon atoms and preferably an acetyl radical, and X and Y, independently of one another, are methylene radicals or sulphur atoms, and Q is either Asp or Asn, A is Asp, Asn, Glu or Gly, B is Phe or Leu, D is Met or Val, E is Gly or Val, G is Asn, Ser or Asp, K is Lys or Glu, and L and M can be any desired amino acid, but L is preferably Ala, Phe, Pro, Glu, Ser, Ile, Leu, Val, Tyr, Hypro, Gln, Hse, Thr, Asp or Asn, and especially preferably is Ala, Val, Leu, Ile, Thr, Asp, Asn, Glu or Gln, and M is preferably Phe, Pro, Hypro, Tyr, Ala, Val, Leu, Ile, Ser, Thr, Asp, Asn, Glu or Gln and $R^3$ is a hydroxyl or amino group or any further desired amino acid, preferably Gly or Tyr, or one of the peptide sequences -Gly-Arg-Arg-Arg-Arg-Asp-Leu-Gln-Ala, -Gly-Arg-Arg-Arg-Arg or -Gly-Lys-Lys-Arg, as well as the homologues and the partial sequences of these peptides, which can be shortened by up to 10 amino acids on the C-terminal end of the chain, and pharmacologically acceptable salts of these peptides for the preparation of pharmaceutical compositions for the treatment of erectile dysfunctions in mammals and preferably in men. The invention also provides pharmaceutical compositions which contain the above peptides, as well as a method of treating erectile dysfunctions in mammals and men by means of the above-mentioned peptides.

The peptamide of general formula (I) is preferably human CGRP.

For the case in which, in a peptide of general formula (II), X and Y simultaneously signify sulphur atoms, besides the preferred intramolecular disulphide bridges, peptides can also be present as dimers by the formation of intramolecular disulphide bridges, in which case a head-head, i.e. parallel, but preferably a head-tail, i.e. anti-parallel, linkage is possible.

According to the international rules of nomenclature, the abbreviations for the above-mentioned amino acids indicate the free acids and the L- and D-configurations but preferably the L-configurations, in which the α-amino group is on the left-hand side and the carboxyl group on the right-hand side. The absence of a hydrogen atom on the α-amino group is indicated by a hyphen on the left side of the abbreviation and the absence of the hydroxyl group in the carboxyl group by a hyphen on the right side.

The present invention is also concerned with the use of compounds of general formula (II) converted for galenical reasons into the pharmacologically acceptable salts. The salts are obtained in the usual manner by neutralization of the bases with inorganic or organic acids. The inorganic acids can be, for example, hydrochloric acid, sulphuric acid, phosphoric acid or hydrobromic acid and the organic acids can be, for example, acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxy-benzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid.

The peptides which contain at least one carboxyl group and at least one basic group, for example an amino group, can also be used in the form of their inner salts.

In addition, those of the above-mentioned peptides which, on the basis of a free carboxyl group, have been converted into metal or ammonium salts, can also be used. The metal salts can be, for example, zinc, iron, sodium, potassium, barium, aluminium, magnesium or calcium salts and the ammonium salts can be the salts with ammonia or organic amines, in which case aliphatic, cycloaliphatic, cycloaliphatic-aliphatic or araliphatic primary, secondary or tertiary mono-, di- or polyamines, as well as heterocyclic bases, can be used, for example alkylamines containing up to 6 carbon atoms in the alkyl moieties, such as triethylamine; hydroxylamines with up to 6 carbon atoms in the alkyl moieties, such as 2-hydroxyethylamine, bis-(2-hydroxyethyl)-amine, 2-hydroxyethyl-diethylamine or tri-(2-hydroxyethyl)-amine; or also basic aliphatic esters of carboxylic acids, such as 4-aminobenzoic acid 2-diethylaminoethyl ester; alkyleneamines, for example 1-ethylpiperidine; cycloalkylamines, such as dicyclohexylamine; or benzylamines, such as N,N'-dibenzylethylenediamine, or also bases of the pyridine type, for example pyridine, collidine or quinoline.

Besides the usual auxiliary, carrier and additive materials, the pharmaceutical compositions according to the present invention contain an effective dosage of compounds of general formula (II) and/or of the salts thereof for the treatment of the said dysfunctions. The dosage depends upon the species, body weight, age, individual state and method of administration.

As forms of administration, there can be used not only parenteral but also topical compositions, for example lotions, creams, solutions, gels, sprays, elastic liquid plasters, transdermal systems or coatings for condoms.

Compositions for parenteral administration contain 0.5 μg to 1 mg and preferably from 5 to 500 μg of the compounds of general formula (II) per dosage unit and can be present in separate dosage unit forms, for example in ampoules or phials. Solutions of the active material are preferably used, especially aqueous solutions and in particular isotonic solutions but also suspensions. These forms of injection can be made available as finished preparations or can first be prepared before use by mixing the active compound, for example in the form of a lyophilisate, optionally with further solid carrier materials, with the desired solvent or suspension agent. Parenteral as well as topical forms can be sterilized and/or optionally contain auxiliary materials, for example preserving agents, stabilizers, wetting agents, penetration agents, emulsifiers, spreading agents, solubilizing agents, salts for the regulation of the osmotic pressure or for buffering and/or viscosity regulators.

Such additives can be, for example, tartrate and citrate buffers, ethanol and complex formers (such as ethylenediamine-tetraacetic acid and the non-toxic salts thereof). For the regulation of viscosity, there can be used, for example, liquid polyethylene oxide, carboxymethylcelluloses, polyvinylpyrrolidones, dextrans or gelatine. Solid carrier materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol).

Oily suspensions for parenteral or topical use can contain vegetable, synthetic or semisynthetic oils, for example liquid fatty acid esters containing 8 to 22 carbon atoms in the fatty acid chain, for example palmitic, lauric, tridecyl, margaric, stearic, arachic, myristic, behenic, pentadecylic, linoleic, elaidic, brassidic, erucic or oleic acid, which are esterified with mono- to trihydroxy alcohols containing up to 6 carbon atoms, for example methanol, ethanol, propanol, butanol, pentanol and the isomers thereof, glycol or glycerol. Such fatty acid esters are, for example, commercially available myglycols, isopropyl myristate, isopropyl palmitate, isopropyl stearate, PEG 6-capric acid, capryl/capric acid esters of saturated fatty alcohols, polyoxyethylene glycerol trioleates, ethyl oleate, wax-like fatty acid esters, such as synthetic duck anal gland fat, coconut fatty acid isopropyl ester, oleyl oleate, decyl oleate, ethyl lactate, dibutyl phthalate, diisopropyl adipate, polyol fatty acid esters and the like. There can also be used silicone oils of differing viscosity or fatty alcohols, for example isotridexyl alcohol, 2-octyldodecanol, cetyl-stearyl alcohol or oleyl alcohol, or fatty acids, for example oleic acid. Furthermore, there can be used vegetable oils, for example castor oil, almond oil, olive oil, sesame oil, cotton seed oil, groundnut oil or soya bean oil. In addition, the mentioned materials have the properties of a spreading agent, i.e. especially good distribution takes place on the skin.

As solvents, gel formers and solubilizing agents, there can be used water or water-miscible solvents. For this purpose, there can be used, for example, alcohols, such as ethanol, isopropanol, benzyl alcohol, 2-octyldodecanol or polyethylene glycols, phthalates, adipates, propylene glycol, glycerol, di- and tri-propylene glycol, waxes, methyl cellosolve, cellosolve, esters, morpholines, dioxan, dimethyl sulphoxide, dimethylformamide, tetrahydrofuran, cyclohexanone and the like.

As film formers, there can be used cellulose ethers which can dissolve or swell not only in water but also in organic solvents and, after drying, form a kind of film, for example hydroxypropylcellulose, methylcellulose, ethylcellulose and soluble starches.

Mixed forms between gel and film formers can also be used. In this case, there are especially used ionic macromolecules, for example sodium carboxymethyl-cellulose, polyacrylic acid, polymethacrylic acid and the salts thereof, sodium amylopectin semiglycolate, alginic acid or propylene glycol alginate as sodium salt, gum arabic, xanthan gum, guar gum or carrageenan.

As further formulation adjuvants, there can be used glycerol, paraffins of varying viscosity, triethanolamine, collagen, allantoin, novantisolic acid and perfume oils.

The use of tensides, emulsifiers or wetting agents can also be necessary for the formulation, for example sodium lauryl sulphate, fatty alcohol ether sulphates, disodium N-lauryl-$\beta$-iminodipropionate, polyoxyethylated castor oil, sorbitan monooleate, sorbitan monostearate, cetyl alcohol, lecithin, glycerol monostearate, polyoxyethylene stearate, alkylphenol polyglycol ethers, cetyl trimethylammonium chloride or monodialkylpolyglycol ether orthophosphoric acid monoethanolamine salts.

Stabilizers, such as montmorillonite or colloidal silicic acids, for the stabilization of emulsions or for the prevention of the breakdown of the active substances, such as anti-oxidants, for example tocopherols or butylhydroxyanisole, or preserving agents, for example p-hydroxybenzoic acid esters, can possibly also be necessary for the preparation of the desired formulations.

For the promotion of the penetration, transdermal formulations preferably contain organic solvents of good skin compatibility, for example ethanol, methylpyrrolidone, polyethylene glycol, oleyl alcohol, octanol, linoleic acid, triacetin, propylene glycol, glycerol, solketal or dimethyl sulphoxide.

The production, filling and sealing of the preparations take place under conventional antimicrobial and aseptic conditions. For topical or transdermal use, the packing preferably consists of separate dosage units for simplification of use and here, too, as in the case of the parenteral forms, possibly for stability reasons, by separate packing of the active materials or of combinations thereof as lyophilisates, optionally with solid carrier materials and the necessary solvents and the like.

A further aspect of the present invention is the use of the compounds of general formula (I) in combination with synergistically-acting substances, for example adenosine, vitamins, for example vitamin A or H, prostaglandins, for example $E_1$, peptides, for example the tetrapeptide Asp-Leu-Gln-Ala, with calcium antagonists, such as nifedipine, verapamil, diltiazem, gallopamil, niludipin, nimodipin, nicardipine, prenylamine, fendiline, terodilin, nisaldipin, nitrendipin or perhexiline. Further combination possibilities exist with $\alpha$-receptor blockers, for example phentolamine methanesulphonate, phenoxybenzamine or minoxidil, or relaxants of the smooth musculature, for example papaverine. The mentioned tetrapeptide Asp-Leu-Gln-Ala can also be used alone or in combination with the mentioned substances for the purpose according to the present invention.

The following Examples are given for the purpose of illustrating the present invention:

EXAMPLE 1

Injection Solution 50 mg human CGRP are dissolved with 750 mg sodium chloride in distilled water, adjusted to pH 3.7 with 1N hydrochloric acid and made up to 100 ml with distilled water and filled into 0.5 ml ampoules.

EXAMPLE 2

Solution for Topical Administration.

A solution for topical administration is prepared from 500 mg CGRP, 2 ml isopropyl myristate and 10 ml ethanol and packed into dosage units of 2 ml.

EXAMPLE 3

Transdermal Plaster 10 g Linoleic acid and 90 g propylene glycol are mixed and 5 g CGRP are dissolved in this mixture. Gauze squares coated on one side with synthetic resin are impregnated with this solution and sealed between aluminium foils.

EXAMPLE 4

Spreadable Gel 94 g purified water are heated to 70° C. and mixed with 10 g CGRP. After the addition of 0.2 g ethyl p-hydroxybenzoate, 5 g methyl hydroxyethyl-cellulose are dispersed in the solution obtained. The mixture is then cooled, while stirring. After cooling, there is obtained a highly viscous gel with a viscosity of 90 Pa.s.

EXAMPLE 5

Oil-in-Water Emulsion

In a first batch, 7 g of a mixture consisting of saturated fatty acids, fatty alcohols, wool wax, mineral oils and non-ionic emulsifiers are homogeneously melted by heating to 70° C. in a water bath, together with 2.5 g polyethylene glycol glycerol fatty acid ester, 3 g cetyl alcohol and 3.0 g isopropyl palmitate. In a second batch, 80 g of purified water are mixed, while stirring, with 3 g propylene glycol and heated to 70° C. The mixture thus obtained is then mixed with 5 g CGRP and 200 mg of a preserving agent. The clear solution obtained is emulsified into the first batch, while stirring at 70° C. The emulsion so obtained is cooled to 40° C. and the loss of water due to evaporation is supplemented. The emulsion is cooled to 30° C. and then packed.

EXAMPLE 6

Liquid Plaster 5 g CGRP are dissolved in a mixture of 5 g benzyl alcohol, 6 g isopropyl stearate or an equal amount of an isopropyl myristate/isopropyl palmitate/isopropyl stearate mixture, 10 g vinylpyrrolidone/vinyl acetate copolymer and 89 g isopropanol. The solution can be packed in separate dosage units for liquid application or can be packed as a spray with conventional propellants.

EXAMPLE 7

Oil-Water Emulsion

According to conventional methods, there is prepared a mixture of 5 g CGRP, 9 g of a mixture of mono- and diglycerides of palmitic and stearic acid, 3 g cetyl stearyl alcohol with about 12 mole ethylene oxide, 10 g 2-octyldodecanol, 5 g very viscous paraffin, 5 g benzyl alcohol and 500 mg PHB ester and made up with diminieralized water to 100 g.

EXAMPLE 8

Cream of Soft Consistency

Such a cream contains, for example, 5 g CGRP, 4 g mono- and diglycerides of palmitin and stearic acid, 4 g cetyl palmitate, 1 g cetylstearyl alcohol with about 12 mole ethylene oxide, 1 g cetylstearyl alcohol with about 30 mole ethylene oxide, 5 g isopropyl myristate/isopropyl palmitate/isopropyl stearate mixture, 0.5 g slightly cross-linked polyacrylic acid of extremely high molecular weight, 0.11 g sodium hydroxide (45%) and 3 g glycerol made up with demineralized water to 100 g.

EXAMPLE 9

Non-Greasy Emulsion

A mixture of 2.5 g decyl oleate, 2.5 g isopropyl myristate, 4 g low viscosity paraffin, 0.9 g polyethylene stearate and 0.6 g sorbitan and glycerol fatty acid esters is stirred for 10 minutes at 70° C. and melted, The molten mixture is added, with stirring, to a solution at 75° C. of 50 g demineralized water, 500 mg CGRP and 100 mg allantoin and cooled to 45° C. At this temperature, there is added a carbopol mucilage of 10 g ethanol, 0.7 g carbopol 934 (weakly cross-linked polyacrylic acid) and 22.95 g demineralized water, which was dispersed with a Turrax stirrer, subsequently swollen for 2 hours and neutralised with 0.15 g of a 45% aqueous solution of sodium hydroxide. Upon reaching 40° C., 1 g collagen is again added thereto. Finally, the crude emulsion, possibly after the addition of 0.6 g of perfume oil, is homogenized at 20° to 25° C. in a high pressure homogenizer.

EXAMPLE 10

Gelatine Solution

For a gelatine solution, 10 $\mu$g CGRP, 150 mg gelatine and 4.7 mg phenol are made up to 1 ml with distilled water and filled in 1 ml amounts into phials.

EXAMPLE 11

Spray

200 $\mu$g CGRP are suspended in a mixture of 3.5 ml Miglycol 812 and 0.08 g benzyl alcohol. This suspension is filled into a container with a measuring valve. 5 ml Freon 12 are now filled into the container under pressure through the valve. By shaking, the Freon is dissolved in the Miglycol-benzyl alcohol mixture.

The effectiveness of the medicaments for the purpose according to the present invention is demonstrated by the following pharmacological investigations:

The necessary in vivo experiments were carried out on seven Cynomolgus monkeys with a body weight of from 4.3 to 8.3 kg under ketamine anaesthesia (30 mg/kg intramuscular). The monkeys were placed in the dorsal position. Under sterile conditions, a 21-G butterfly cannula was placed bilaterally into the distal erectile tissue. For the recordal of the intracavernal pressure, a needle was connected with a Statham pressure converter (model P23 BC) and the other used for the intracavernous injection or perfusion. The penile tumescence was monitored visually by two observers and recorded. A classification of the tumescence took place according to the parameters: E 0=no tumescence; E 1=slight tumescence; E 2 =partial tumescence; E 3=complete tumescence. A flowthrough measurement of the cavernal arteries was carried out by means of ultrasonics on four monkeys. The pulse and blood pressure were measured by means of Doppler measurement (Parks Medical Electronics) on the radial artery with the help of a paediatric blood pressure cuff.

In a pilot study, 50, 500 and 2500 ng h-CGRP (Sigma Chemical Co., St. Louis, Mo.) were injected intracavernously into two monkeys. 50 ng induced only a slight, brief tumescence. 2500 ng h-CGRP lowered the systemic blood pressure to below 35 cm $H_2O$. The erectile behaviour was thereby, however, similar to the 500 ng administration but longer lasting. Therefore, the further investigations were carried out with dosages of 500 ng and, for ensuring the reproducability, repeated on a second day.

First, after the intracavernous injection, an increase of the arterial flow was observed, a tumescence of the penis took place and, one minute thereafter, an increase of the intracavernous pressure. Before the injection, a measurement of the flow rate of the cavernous artery was not possible. On average, there was observed a maximum flow rate 4 minutes after the CGRP injection, which again decreased after 3 to 4 minutes. 32 to 69 minutes (49 minutes on average) after the intracavernous injection, arterial flow could no longer be ascertained.

A tumescent increase of the penis was observed 30 to 60 seconds after the CGRP injection and maximum tumescence and elongation (E 3) 4 minutes after the injection to the time of the maximum arterial flow up to 15 minutes after the injection. The tumescence then decreased stepwise until, after an average value of 32 minutes, no difference was observed between the tumescence before and after the injection. The intracavernous pressure before the CGRP injection was 24 to 45 (average 34) cm $H_2O$, 90 to 120 seconds after the injection 62 to 94 (average 78) cm $H_2O$ and, after 4 minutes, decreased within 1 minute to 40 to 54 (average 47) cm $H_2O$. This pressure then decreased within 36 minutes to the initial value.

I claim:

1. A method of treating erectile dysfunctions in mammals, which comprises: administering to said mammal a pharmaceutical composition comprising a therapeutically effective amount of an active agent selected from the group consisting of (a) a calcitonin gene-related peptide having the general formula:

$$R^1-CH---CH_2----X----Y----CH_2$$
$$\phantom{R^1-}|\phantom{CH---CH_2----X----Y----}|$$
$$\phantom{R^1-}CO-Q-Thr-Ala-Thr-NHCH-CO-Val-Thr-$$

—His—Arg—Leu—Ala—

A—B—Leu—Ser—Arg—Ser—Gly—Gly—D—E—Lys—G—

—Asn—Phe—Val—

-continued
Pro—Thr—Asn—Val—Gly—Ser—K—L—M—$R^3$ wherein $R^1$ is either a hydrogen atom or a radical of the general formula $R^2$—T— wherein T is Ala or Ser and $R^2$ is a hydrogen atom or an acyl radical containing up to 4 carbon atoms; X and Y are, independently, methylene radicals or sulphur atoms; Q is Asp or Asn; A is Asp, Asn, Glu or Gly; B is Phe or Leu; D is Met or Val; E is Gly or Val; G is Asn, Ser or Asp; K is Lys or Glu; L is selected from the group consisting of Ala, Phe, Pro, Glu, Ser, Ile, Leu, Val, Tyr, Hypro, Gln, Hse, Thr, Asp, and Asn; M is selected from the group consisting of Phe, Pro, Hypro, Tyr, Ala, Val, Leu, Ile, Ser, Thr, Asp, Asn, Glu, and Gln; and $R^3$ is a hydroxyl group, an amino group, or a peptide of the sequence -Gly-Arg-Arg-Arg-Arg-Asp-Leu-Gln-Ala, -Gly-Arg-Arg-Arg-Arg, or -Gly-Lys-Lys-Arg; (b) a peptide having the formula of (a) in which up to 10 amino acids of the C-terminal end of the peptide are omitted; and (c) pharmaceutically acceptable salts of the peptides defined in (a) or (b).

2. The method of claim 1, wherein L is selected from the group consisting of Ala, Val, Leu, Ile, Thr, Asp, Asn, Glu, and Gln.

3. The method of claim 1, wherein said calcitonin gene-related peptide is present in an amount of 0.5 µg to 5 mg.

4. The method of claim 1, wherein said pharmaceutical composition further comprises an active material selected from the group consisting of adenosine, vitamins, protaglandins, calcium antagonists, α-receptor blockers and relaxants of the smooth musculature, and mixtures thereof.

5. A method of treating erectile dysfunctions in mammals, which comprises: administering to said mammal a pharmaceutical composition comprising a therapeutically effective amount of a human calcitonin gene-related peptide having the general formula:

H—Ala—Cys—Asp—Thr—Ala—Thr—Cys—Val—Thr—His—Arg—

Leu—Ala—Gly—Leu—Leu—Ser—Arg—Ser—Gly—Gly—Val—Val—

Lys—Asn—Ans—Phe—Val—Pro—Thr—Asn—Val—Gly—Ser—Lys—

Ala—Phe—$NH_2$.

6. The method of claim 5, wherein said calcitonin gene-related peptide is present in an amount of 0.5 µg to 5 mg.

7. The method of claim 5, wherein said pharmaceutical composition further comprises an active material selected from the group consisting of adenosine, vitamins, prostaglandins, calcium antagonists, α-receptor blockers and relaxants of the smooth musculature, and mixtures thereof.

* * * * *